United States Patent [19]

Bailey

[11] Plant 4,012

[45] Jan. 25, 1977

[54] ROSE PLANT

[75] Inventor: Dorothy Jean Searles Bailey, Bakersfield, Calif.

[73] Assignee: San Joaquin Rose Co., McFarland, Calif.

[21] Appl. No.: 661,277

[22] Filed: Feb. 25, 1976

[51] Int. Cl.[2] ..... A01H 5/00

[52] U.S. Cl. ..... Plt./11

[58] Field of Search ..... Plt./11

*Primary Examiner*—Robert E. Bagwill

*Attorney, Agent, or Firm*—Vincent G. Gioia

[57] ABSTRACT

A new and distinct variety of rose plant of the hybrid tea class, substantially as shown and described, characterized particularly by flowers of unique bicolor tonality combining red and cerise colors with yellow tone shadings on the obverse of the petals with red streaking and red and yellow coloring on the reverse, high center, spiral petal formation and by a plant of upright habit of growth having an abundance of leathery foliage starting yellow green as new and darkening on maturity.

1 Drawing Figure

The present invention relates to a new and distinct variety of rose plant of the hybrid tea class, which was originated by my crossing the rose variety known as "Granada" as seed parent with the rose variety known as "Peace", as pollen parent.

Among the novel characteristics possessed by this new variety which distinguish it from its parents and all other varieties of which I am aware are: (1) flowers of bicolor tonality which combine red and cerise colors with yellow shadings on the obverse of the petals with red streaking and red and yellow tones on the reverse, (2) flowers of high center and spiral form which are very long lasting on the plant, (3) abundant foliage of leathery texture, and (4) few thorns. Asexual reproduction by budding of the new variety as performed in Kern County, Calif., shows that the foregoing and other distinguishing characteristics come true to form and are established and transmitted through succeeding propagations.

A main distinguishing feature of the new and improved rose variety is its unusual, attractive coloring of the flowers which are produced in good size and in large quantities. In addition, this new variety does not possess the same susceptibility to diseases, such as "mildew", which is typical of its seed parent "Granada".

Flowers of this new variety are usually borne singly, opening as high centered buds with recurling petals as the bloom matures, and maintaining the high center affect as they age. Petals are of a satiny appearance and are regularly arranged, however, the flowers are long lasting on the plant and after cutting. The abundant, thick, leathery foliage provides a fine background for the unusual distinctive and attractive bicolor tonality of the blooms.

The accompanying drawing shows typical specimens of the flowers and vegetative growth of the new variety in different stages of development and as depicted in color as nearly true as it is reasonably possible to make the same in a color illustration of this character.

The following is a detailed description of my new variety, with color terminology in accordance with the Royal Horticultural Society Color Chart (RHSCC). The terminology used in color description herein refers to plate numbers in the aforementioned color chart, e.g., "45B" is plate 45B of the Royal Horticultural Society Color Chart.

Parentage: Seedling.

*Seed parent.*—"Granada".

*Pollen Parent.*—"Peace".

Class: Hybrid tea.

The following observations are made of specimens grown outdoors at Kern County, Calif., during the month of June.

FLOWER

Blooming Habit: Continuous.

Bud:

*Size.*—Medium.

*Form.*—Long pointed, recurling bud.

*Color.*—When sepals first divide: Near 53B on edge of petal. When petals begin to unfurl: Basic color of petal 13C in bud with 53B on inner edge of petals. When half-blown: inside of petals — 13D with overlay of 45C washing on inside petals; reverse side of petals — 12C with streaking of 45B + 45C + 46B.

*Sepals.*—Narrow, pointed, smooth, recurling freely before petals recurl. Color: inside — 191B; outside — 138B.

*Calyx.*—Color—138B with 178B streaking at base. Shape — Pear; Size — Small; Aspect — Smooth. Odor when rubbed — fruity.

*Peduncle.*—Length — Medium; Aspect — Average Caliper. Strength — Erect; smooth, few gland-tipped cilia; few prickles. Color — 138B.

Bloom:

*Size.*—Average size when fully expanded 4½ to 5 inches.

*Borne.*—Singly.

*Form.*—High centered, petals recurl well as flower opens; open flower retains high center effect.

*Petalage.*—Number of petals under normal conditions — about 42

*Color.*—Center of flower — blend of 13C + 53B. Outer petals — blend of 13C + 45C. Base of petals — 13C. Inside of petals — 13C washed with 45C. Reverse of petals — 12C streaked with 45B, 45C and 46B. General tonality from a distance — multicolor blending of reds and yellow colors described above.

Petals:

*Texture.*—Medium.

*Appearance.*—Satiny.

*Form.*—Outside round with some petals having small point at apex.

*Arrangement.*—Regularly arranged, shingle-like.

*Petaloids in center.*—Few, large.

*Persistence.*—Drop off clean.

*Fragrance.*—Light old rose.

*Lasting quality.*—Long lasting on the plant and as a cut flower.

REPRODUCTIVE ORGANS

Stamens, Anthers: Medium size, many.

*Arrangement.*—Regularly arranged around styles.

*Color.*—Light orange — yellow — 17B.

Stamens, filaments (threads): Medium length.

*Color.*—Yellow-orange 20A with small red blotching on tube openings of 34A.

Pollen: Color — 22A yellow-orange.

Styles: Bunches; uneven length; medium length; thin.

Stigmas: Color — Yellowish white 11D.

Ovaries: All enclosed in calyx.

Hips: Shape — few, small, globular. Color — 25B when mature.

PLANT

Form: Hybrid Tea.

Growth: Vigorous, compact. Height attained: 3 to 3½ ft. during normal growing season.

Foliage: Compound of 5 to 7 leaves.

*Size.*—Medium.

*Quantity.*—Abundant.

*Color.*—New foliage: upper side — 148A; under side — 148C with upper surface; and under side veins showing reddish purple 71B. Old foliage: upper side — 137A; under side — 138B.

*Shape.*—Oval.

*Texture.*—Upper side — thick, leathery; under side — soft, dull.

*Edge.*—Serrated.

*Serration.*—Small and regularly arranged around leaf.

*Leaf stem.*—Color — 138A; under side — 138B.

*Stipules.*—Medium length; slightly bearded, turned out at an angle or more than 45°.

Wood:

*New Wood.*—Color — 137C with purple red cast 183A. Bark: Smooth.

*Old Wood.*—Color — 137B; very little mottling. Bark: Smooth.

Thorns:

*Thorns.*—Quantity: on main stalks from base — few; on laterals from stalk — very few. Form: narrow base with point curved downward. Length: small. Color when young — 138B green tipped with 71B reddish purple. Position: Regular.

*Prickles.*—Quantity: on main stalks — few; on laterals — none.

*Short Needles.*—Quantity — None; on main stalks — none; on laterals — none.

Plant's Disease Resistance: Mildew — good. Blackspot — good. Rust — good.

Winter Hardiness: Very hardy.

I claim:

1. A new and distinct variety of rose plant of the hybrid tea class, substantially as shown and described, characterized particularly by flowers of unique bicolor tonality combining red and cerise colors with yellow tone shadings on the obverse of the petals with red streaking and red and yellow coloring on the reverse, high center, spiral petal formation and by a plant of upright habit of growth having an abundance of leathery foliage starting yellow green as new and darkening on maturity.

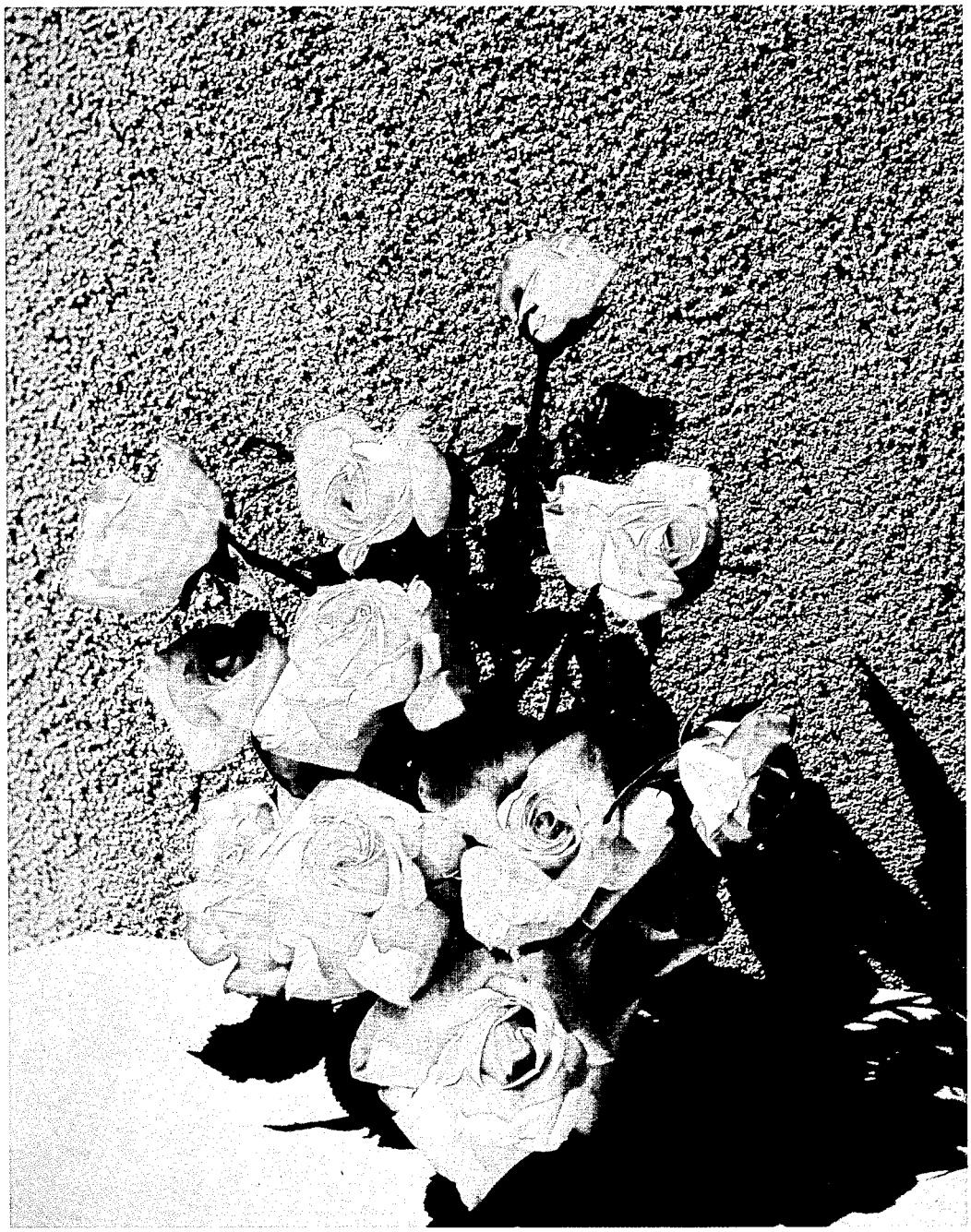

* * * * *